US00PP11372P

United States Patent [19]

Jelenkovic et al.

[11] Patent Number: Plant 11,372

[45] Date of Patent: May 2, 2000

[54] STRAWBERRY PLANT 'NJ8826-11'

[75] Inventors: Gojko L. Jelenkovic, Piscataway; Joseph A. Fiola, Whiting, both of N.J.

[73] Assignee: Rutgers University, New Brunswick, N.J.

[21] Appl. No.: 09/034,201

[22] Filed: Mar. 3, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 7,160 2/1990 Johnson, Jr. et al. ..... Plt./208

P.P. 8,649 3/1994 Sjulin et al. ..... Plt./208

*Primary Examiner*—Howard J. Locker
*Assistant Examiner*—Wendy A. Baker
*Attorney, Agent, or Firm*—Synnestvedt & Lechner LLP

[57] ABSTRACT

A new and distinct cultivar of strawberry plant (*Fragaria*× *ananassa*) named 'NJ8826-11', which is a short day cultivar similar to 'Earliglow', but which is exceptional for its combination of very early season harvest of attractive and extra large fruit, with high productivity, good plant vigor, and disease resistance. The plant is well adapted to matted-row, ribbon-row, and high density planting systems, and performs consistently in diverse environments. The fruit size is much larger than that of 'Earliglow', the major cultivar in its season, and the fruit flavor is good.

5 Drawing Sheets

BACKGROUND OF THE NEW PLANT

The present invention relates to the discovery and asexual propagation of a new and distinct short day type cultivar of strawberry plant (*Fragaria*×*ananassa*), which resulted from crossing the selection 'NJ8219-2' as the seed parent and the selection 'MDUS5180' as the pollen parent in 1988 at the Rutgers University Plant Science Greenhouses in New Brunswick, N.J. Both parent plants are unpatented, non-commercial varieties. The complete pedigree of 'NJ8826-11' is shown below:

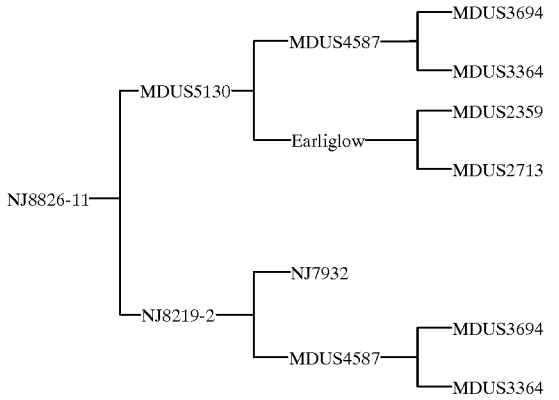

The new cultivar has been designated as 'NJ8826-11'. This specific clone was the eleventh of sixteen selections in the progeny, and was discovered by Gojko L. Jelenkovic and Joseph A. Fiola in June, 1990 at Rutgers Plant Science Farm 3 in New Brunswick, N.J. The new 'NJ8826-11' plant was recognized as being distinguishable from other known commercial strawberry plant varieties in that it is a very early variety, as early or earlier than the known (unpatented) 'Earliglow' variety, but at the same time the new variety demonstrates in its early season much larger fruit than any other commercial strawberry variety.

The new plant was designated 'NJ8826-11' in the breeding records and was first asexually propagated, by runners, by Gojko L. Jelenkovic in about July, 1990 at Rutgers Plant Science Farm 3. It was recognized and selected as a distinctive and superior clone by Joseph A. Fiola based on extensive testing at the Rutgers Fruit Research and Extension Center in Cream Ridge, N.J. The new cultivar was subsequently tested extensively at the Rutgers Fruit Research and Extension Center in Upper Deerfield, N.J. and the Snyder Research and Extension Center in Pittstown, NJ. Limited grower testing started in 1994. The new cultivar has shown to be stable in its distinguishing characteristics over several generations, through successive asexual propagations using runners.

DETAILED BOTANICAL DESCRIPTION OF THE NEW PLANT

Figure 1:
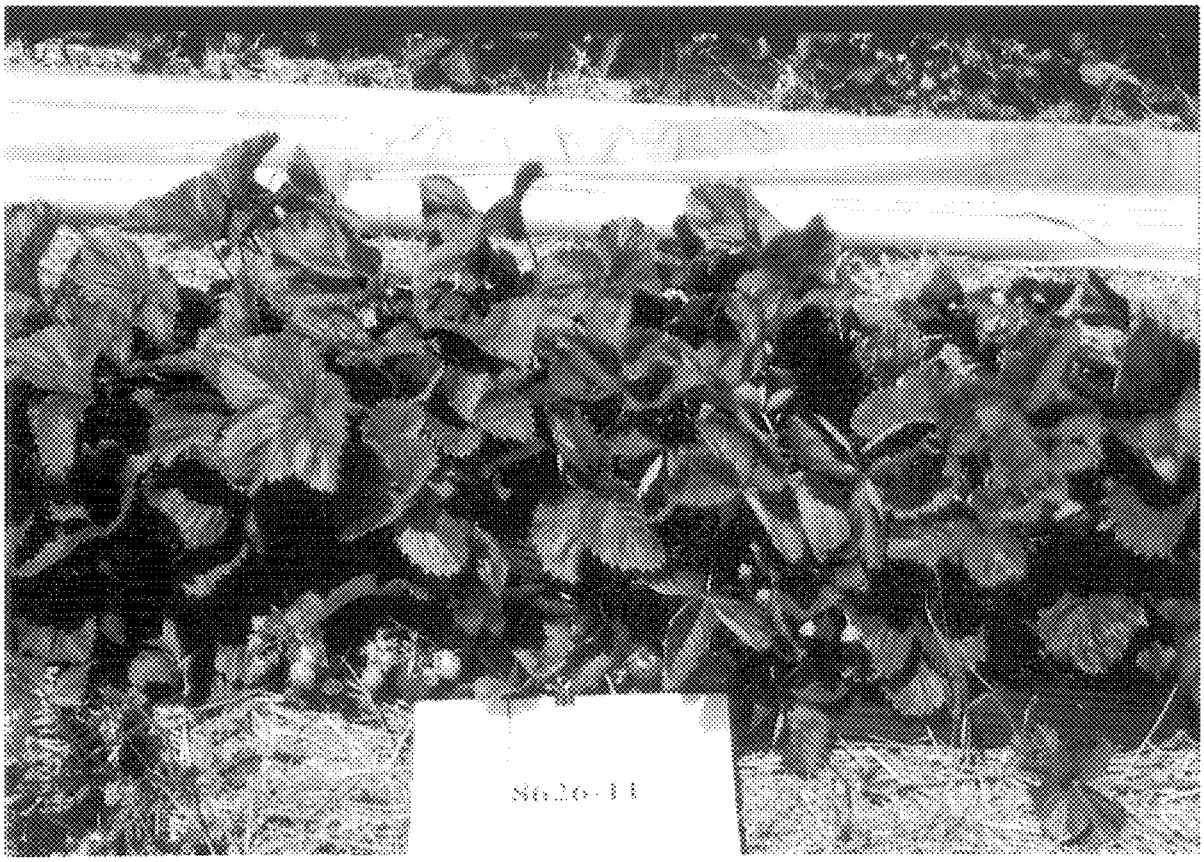
FIG. 1 illustrates a typical example of a plot of the new cultivar, illustrating the vegetative habit in a high density plasticulture system.
Figure 2:
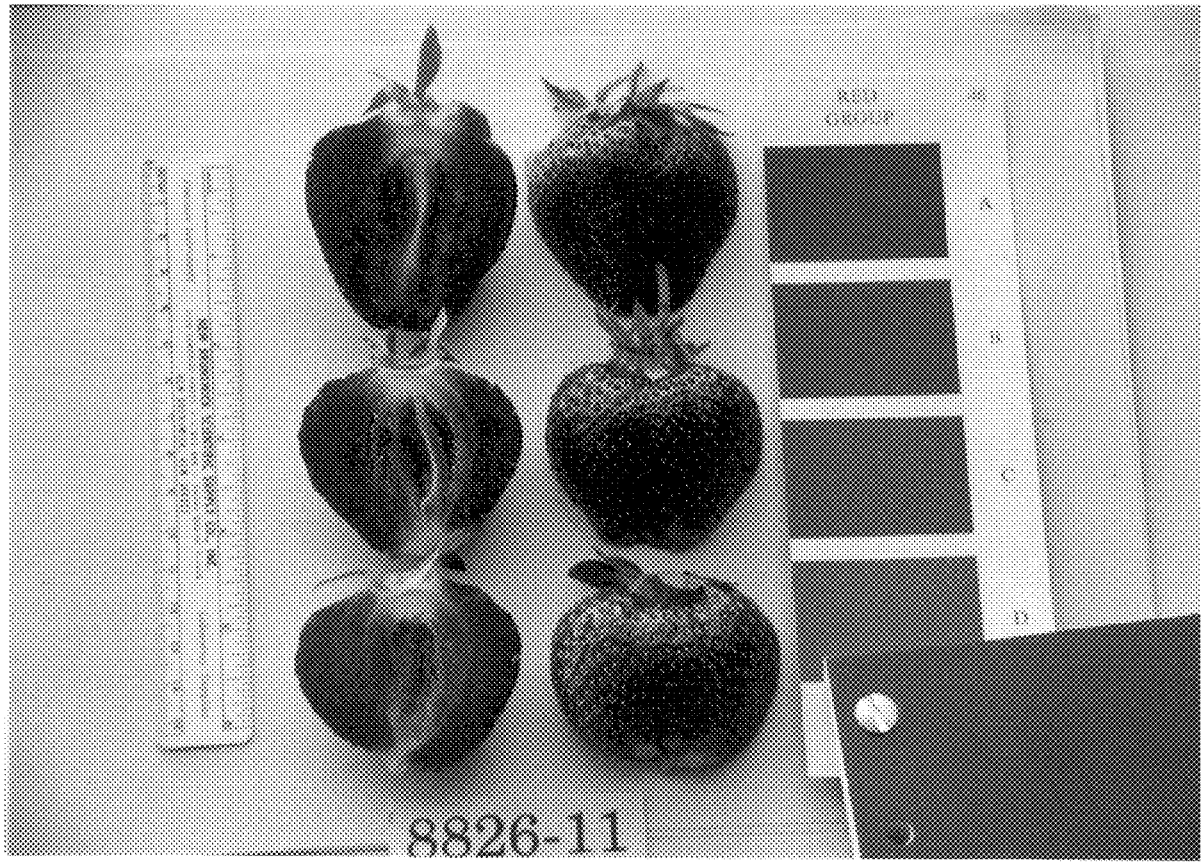
FIG. 2 illustrates a typical example of the strawberry fruit of the new cultivar, disclosing the fruit's conic shape, length, width, external flesh and skin color, internal flesh color, seed color and prominence, and calyx size and pose.
Figure 3:
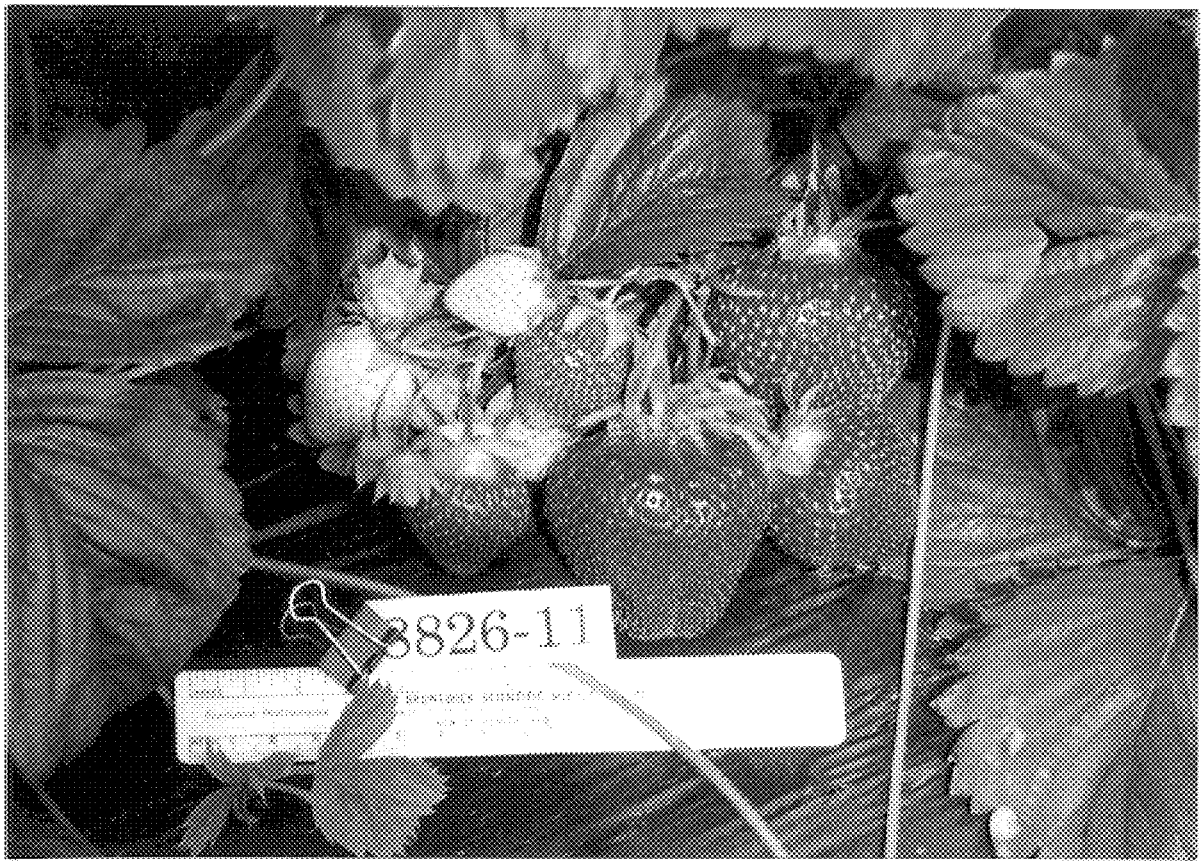
FIG. 3 depicts a raceme of the fruit of the new cultivar, with reference to a 6-inch (15 cm.) ruler.
Figure 4:
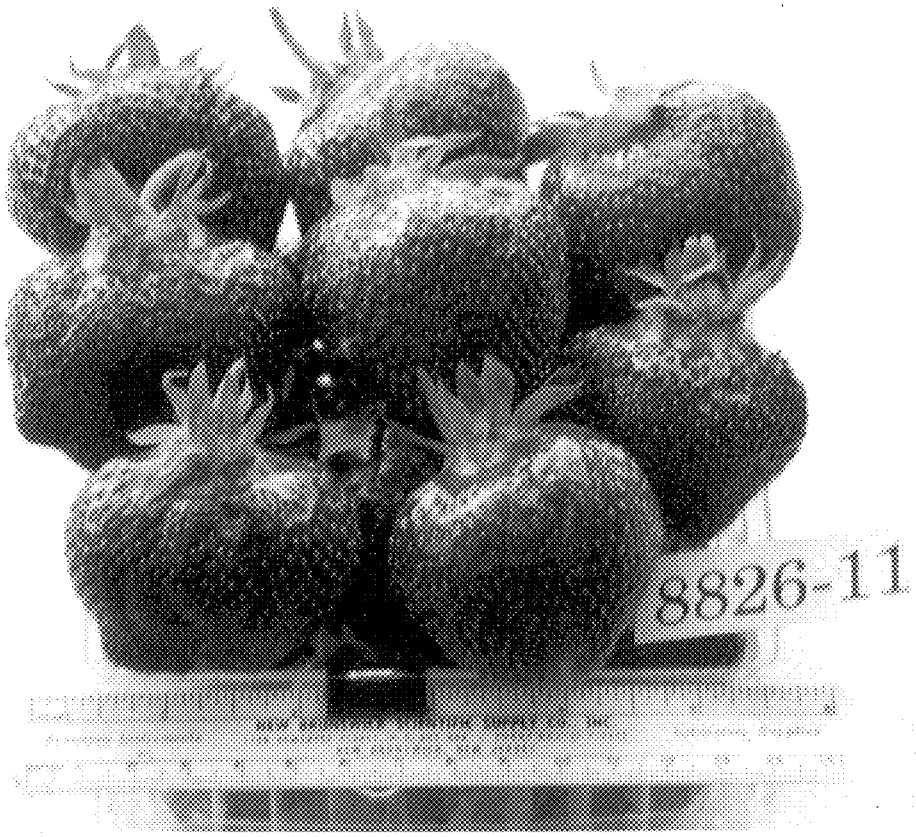
FIG. 4 illustrates a quart of primary fruits of the new cultivar, with reference to a 6-inch (15 cm.) ruler.
Figure 5:
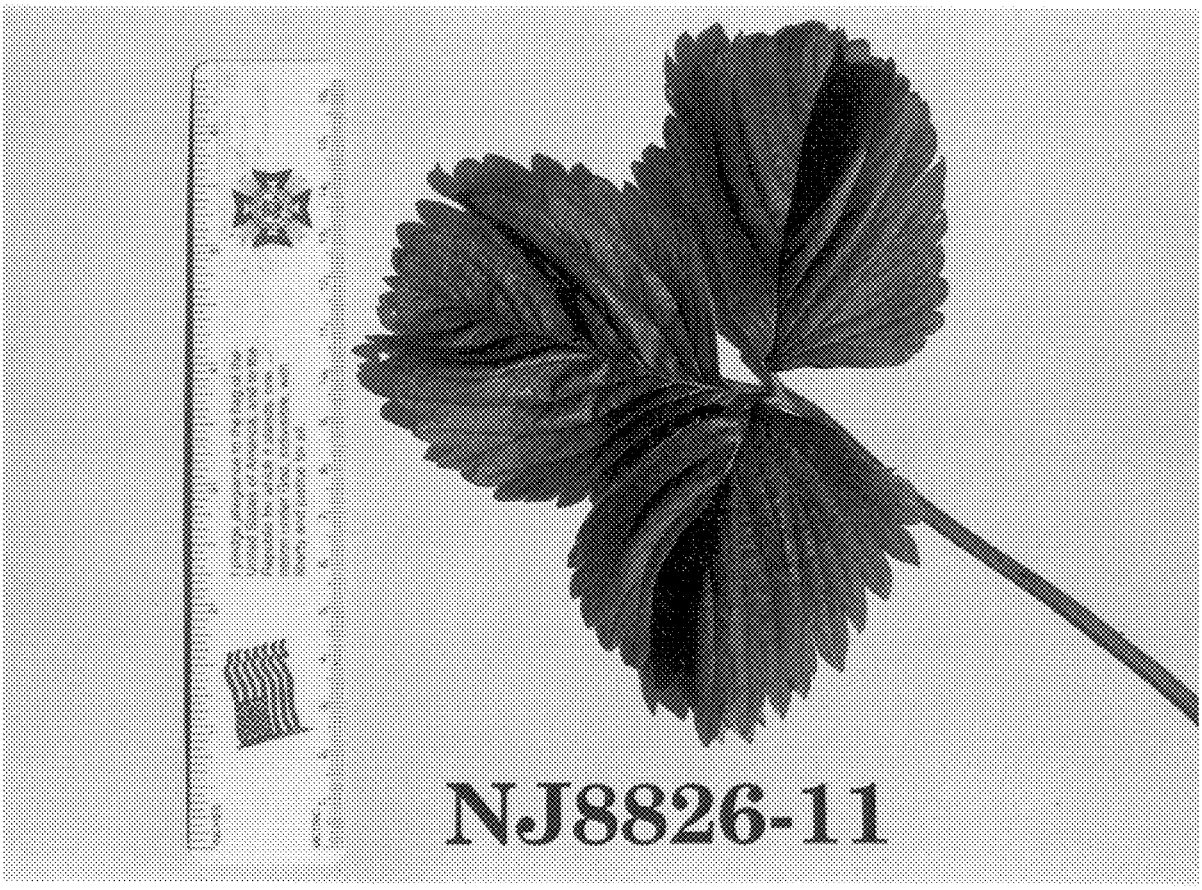
FIG. 5 illustrates a typical trifoliate leaf of the new cultivar, with reference to a 6-inch (15 cm.) ruler.

The following detailed description of the new 'NJ8826-11' plant is based upon observations made of the plants grown in Cream Ridge, N.J., during about the months of April through June. It is believed that this description will apply to 'NJ8826-11' cultivar plants grown in similar conditions of soil and climate elsewhere.

Throughout this specification, color names beginning with a small letter signify that the name of that color as used in common speech is aptly descriptive. Color names beginning with a capital letter designate color values based on The R.H.S. Colour Chart published by The Royal Horticultural Society of London, England.

Plants and foliage: The vegetative habit of the new plant is one of high overall vigor, with branching and runnering to form a high density matted-row. It produces few but large crowns when planted in high density on plastic. It is also well adapted to ribbon-row culture.

The new plant appears to be generally well adapted to, and has performed exceptionally well on, heavier soils in the northern locations of New Jersey.

The trifoliate leaves are semi-erect to erect, petioles bearing scattered hirsute hairs; 3 leaflets ovate-orbicular, margins serrate, apices round, bases of terminal leaflets cuneate and 2 lateral leaflet bases slightly to moderately oblique; upper leaflet surface lightly and scattered sericeous or nearly glabrous; lower leaflet surface lightly and scattered sericeous hairs mostly on veins; all leaflet hairs appressed; petiolules lightly hirsute. Adaxial and abaxial leaf surfaces are medium green in coloration and typical of the species. Typical measurements for the trifoliate leaves are shown in Table 5.

Isozymes in leaf extracts: Isozyme patterns for glucose phosphate isomerase (GPI), leucine amino peptidase (LAP), and phosphoglucomutase (PGM) show banding patterns for this genotype (Table 4).

Disease and pest reaction: The foliage has good leaf spot and leaf scorch resistance, and will tolerate powdery mildew. The plant has been screened for resistance against strains A-1, A-2, A-3, A-4 and A-6 of Phytophthora, which causes red stele. The plants have also shown good field resistance to Verticillium wilt.

Flowering, fruit, and production characteristics: The plant flowers over a short period with the majority of flowers opening about the same time as the known (unpatented) 'Earliglow' variety, about the last week in April. Flowers are white in coloration and typical of the species. Fruit are numerous, very large, and borne on medium length trusses. In particular, the primary peduncle (range 80–110 mm) branches to a group of pedicels (range 30–70 mm) supporting the primaries, secondaries, tertiaries, etc.

The strawberry fruit is very attractive, brightly colored, with high gloss. Primary fruit are very large, with secondary and tertiary fruit also maintaining very good commercial size. The largest individual primaries of a harvest can weigh in excess of 50 grams/fruit. Seed are yellow to orange, typical of the species, and set flush or slightly raised above the berry surface. The fruit has a slight shoulder and the calyx is about 14.1 mm in diameter and is bright green, typical of the species, attractive and slightly reflexed.

The berry skin has good abrasion resistance and the flesh is very firm. The berry color is bright, deep red (Red 45A). The internal color is bright red (Red 46A), with little gradation towards the center. The fruit has good sweet/ acid balance, and medium strawberry flavor intensity.

TABLE 1

Yield parameters of 'NJ8826-11', relative to other cultivars and selections of the early harvest season, in a matted-row production system at Cream Ridge, New Jersey; data is combined means of 1994 and 1995.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| NJ8607-2 | 6 | 75 | 1590 | 11046 | 16.5 | 12.2 |
| NJ8608-1 | 7 | 55 | 1350 | 8610 | 13.9 | 11.6 |
| NJ8614-2 | 7 | 65 | 1100 | 9170 | 16.3 | 12.9 |
| NJ8826-11 | 7 | 75 | 1788 | 9380 | 20.7 | 13.4 |
| Earliglow | 7 | 80 | 2280 | 9400 | 11.8 | 9.6 |
| Annapolis | 6 | 85 | 740 | 5350 | 14.0 | 11.0 |

*Plant vigor ratings are determined through a rating of the vigor of the plant on a subjective scale of 10 (plant extremely weak) to 90 (plant strong, vigorous, filling in predetermined production area).

**Data obtained by weighing a random selection of 20 fruit from a plot at each harvest.

***Refers to the primary or first harvested berries.

TABLE 2

Yield parameters of 'NJ8826-11', relative to other cultivars and selections of the early harvest season, in a plasticulture system at Cream Ridge, New Jersey; data is combined means of 1994 and 1995.

| | | Yield | | Berry Wt.** | |
|---|---|---|---|---|---|
| Genotype | Plant Vig* | Early (lb/A) | Total (lb/A) | Prim*** (g) | Avg (g) |
| NJ8826-11 | 67 | 1440 | 6960 | 14.5 | 11.0 |
| NJ8607-2 | 65 | 660 | 6110 | 14.1 | 11.4 |
| NJ8608-1 | 63 | 760 | 6940 | 13.1 | 10.1 |
| NJ8614-2 | 65 | 740 | 7530 | 15.7 | 12.3 |
| Chandler | 79 | 330 | 9790 | 14.2 | 11.5 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 3

Mean berry length (L), width (W), and girth (G) for 'NJ8826-11' and other cultivars; data from 1995.

| Genotype | Length (mm) | Width (mm) | Girth (mm) |
|---|---|---|---|
| NJ8607-2 | 35 | 37 | 31 |
| NJ8826-11 | 40 | 47 | 40 |
| NJ8614-2 | 36 | 39 | 26 |
| NJ8608-1 | 43 | 37 | 33 |
| Chandler | 37 | 35 | 28 |

TABLE 4

Isozymes patterns for leaf extracts for glucose phosphate isomerase (GPI), leucine amino peptidase (LAP), and phosphoglucomutase (PGM).

| Genotype | GPI | LAP | PGM |
|---|---|---|---|
| NJ8826-11 | A6 | B3 | C2 |
| NJ8614-2 | A1 | B3 | C3 |
| NJ8607-2 | A1 | B3 | C3 |
| Chandler | A1 | B3 | C1 |

TABLE 5

Typical measurements for length and width of trifoliate leaves of 'NJ8826-11'

| | | 1° leaf | | 2° leaves | |
|---|---|---|---|---|---|
| | | Length (mm) | Width (mm) | Length (mm) | Width (mm) |
| Average | | 82 | 68 | 72 | 66 |
| Range: | high | 95 | 78 | 85 | 75 |
| | low | 75 | 60 | 70 | 60 |

We claim:

1. A new and distinct strawberry plant named 'NJ8826-11', as herein illustrated and described.

* * * * *